(12) United States Patent
Nasman

(10) Patent No.: US 7,037,997 B1
(45) Date of Patent: May 2, 2006

(54) VINYL MONOMER, SUPPORT MATRIX AND ITS PREPARATION

(75) Inventor: Jan Nasman, deceased, late of Alunda (SE); by Rose Nasman, legal representative, Vasa (FI); by Harry Nasman, legal representative, Vasa (FI)

(73) Assignee: GE Healthcare Bio-Sciences AB, Uppsala (SE)

( * ) Notice: Subject to any disclaimer, the term of this patent is extended or adjusted under 35 U.S.C. 154(b) by 408 days.

(21) Appl. No.: 09/979,444

(22) PCT Filed: Jun. 6, 2000

(86) PCT No.: PCT/EP00/05194

§ 371 (c)(1),
(2), (4) Date: Sep. 3, 2002

(87) PCT Pub. No.: WO00/75128

PCT Pub. Date: Dec. 14, 2000

(30) Foreign Application Priority Data

Jun. 6, 1999 (SE) .................................. 9902134

(51) Int. Cl.
*C08F 212/14* (2006.01)

(52) U.S. Cl. .................... 526/334; 526/286; 526/312; 526/336; 526/347; 525/328.3; 525/328.5; 525/328.9; 521/146; 521/147; 428/402

(58) Field of Classification Search ............... 526/286, 526/312, 334, 347, 336; 521/146, 147; 428/402; 549/449, 451, 430; 564/349, 374, 391; 568/46, 568/583, 593, 592, 662; 525/328.3, 328.5, 525/328.9

See application file for complete search history.

(56) References Cited

U.S. PATENT DOCUMENTS 3,041,319 A * 6/1962 Abramo .................... 526/307.5

(Continued)

FOREIGN PATENT DOCUMENTS

EP  0 878 491 A  11/1998

(Continued)

OTHER PUBLICATIONS

Wulff, G., et al. "The Synthesys of Polymerizable Sugars" Macromolecular Chem. Phys., vol. 197, 1996, pp. 259-274 XP002147653.

(Continued)

*Primary Examiner*—Fred Teskin
(74) *Attorney, Agent, or Firm*—Yonggang Ji

(57) ABSTRACT

A vinyl monomer of the structure R—B—Ar(—CH═CH$_2$)$_n$ (1) in which Ar is an aromatic ring (arylene group); n is an integer >0, in particular one or two; B is a bridge structure; R is a (C$_{2-30}$)-hydrocarbon group carrying two or more protected or unprotected hydroxy groups. The monomer is characterized in that B comprises a chain of atoms linking R to Ar and consisting of 1–10 atoms selected from carbons and the heteroatoms ether oxygen, thioether sulphur or amino nitrogen, with the proviso that the terminal atom in B which is attached to R is one of the heteroatoms. A method for producing a polymer support matrix in which the vinyl-monomer is one of the monomeric units. The support matrix as such is also claimed. The preferred method for producing the support matrices involves suspension polymerisation, the preferred form of matrix is beads. The matrix is cross-linked

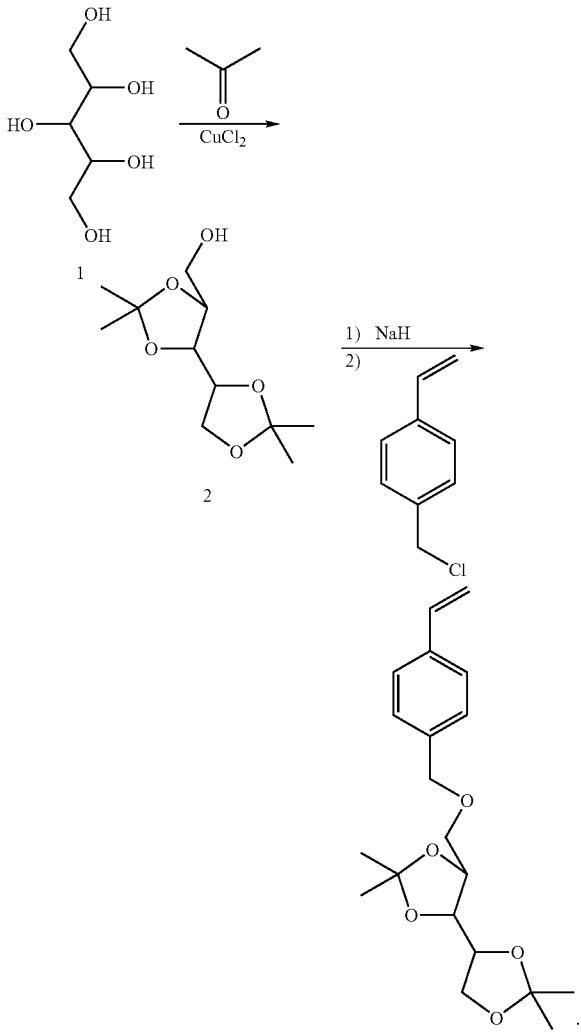

11 Claims, 1 Drawing Sheet

U.S. PATENT DOCUMENTS

| | | | | |
|---|---|---|---|---|
| 3,079,369 A | * | 2/1963 | Abramo | 526/334 |
| 5,731,395 A | * | 3/1998 | Tsuno | 526/334 |
| 5,880,240 A | * | 3/1999 | Tsuno | 526/334 |

FOREIGN PATENT DOCUMENTS

| | | |
|---|---|---|
| JP | 05 086144 A | 4/1993 |
| JP | 05 287685 A | 11/1993 |
| JP | 08 104651 A | 4/1996 |
| WO | WO 97/31026 A | 8/1997 |

OTHER PUBLICATIONS

Chung, D. C., et al., "Polymerizable Amphiphiles" Makromolekulare Chemie, vol. 178, 1977, pp. 691-700 XP002147654.

Klavins, M., et al. "High-Molecular Weight Catalysts in Oragnic Synthesis. XI. New Open-Chain Analogs of Polymer-Supported Crown Ethers in Oragnic Synthesis" Chemical Abstracts Service, Columbus, Ohio US Database Accession No. 107:133589 XP002147655.

* cited by examiner

VINYL MONOMER, SUPPORT MATRIX AND ITS PREPARATION

TECHNICAL FIELD

This invention concerns novel vinyl aromatic monomers having a polyhydroxy moiety attached at a ring atom in the aromatic ring. The monomers are preferably vinyl benzenes such as styrenes. The hydroxy groups may be protected or unprotected. The invention also concerns a method for the manufacture of a support matrix comprising a polymeric hydrocarbon backbone [—$(CH_2CH_2)_n$—] to which there are attached (a) hydrocarbon groups (Rs) replacing a respective hydrogen in the backbone and comprising one or more hydroxy groups and an aryl group attaching the hydrocarbon group to the backbone, and (b) interchain or intrachain cross-linking structures replacing hydrogens in the backbone.

The novel monomers can be used for the manufacture of support matrices of the invention. The monomers in protected form are particularly well fitted for the manufacture of beads (spheres or spheroids) by emulsion polymerisation, and in particular suspension polymerisation.

This kind of support matrices can be used in adsorption and partition processes, such as liquid chromatography, in solid phase organic synthesis, and in cell culturing. They can also be used as support matrices in reactors for immobilized catalysts, such as enzymes and other applications utilizing cross-linked support matrices. Appropriate support matrices are in form of monolithic plugs/membranes or particles, such as beads, and may be non-porous or more preferably porous.

By the term heteroatom is only contemplated oxygen, nitrogen and sulphur.

TECHNICAL BACKGROUND

Styrenes having a polyhydroxy group bound to one of its ring atoms have previously been described and used for the manufacture of polymers/copolymers. The monomers have been used with their hydroxy group being present in either protected or unprotected form:

Wulff et al., Macromol. Chem. Phys. 199 (1998) 141–147;
Wulff et al., Polymer Preprint 39 (1998) 124–125;
Loykulnant et al., Macromolecules 31(26) (1998) 9121–9126;
Hashimoto et al., J. Polymer Science Part A, Polymer Chemistry 37 (1999) 303–312);
Minoda et al., Macromolecules 99 (1995) 189-;
Ohno et al., Macromolecules 21 (1998) 751-).

The monomers of the kind discussed above have been relatively cumbersome to synthesize and/or contain groups that may lead to undesired and/or uncontrollable reactivities in support matrices obtained by polymerisation of the monomers. Neutralization of these kinds of negative reactivities requires further chemical modifications of the matrices.

The polymers previously obtained by polymerisation of the monomers discussed above have been non-cross-linked and water-soluble which are features that one avoid in support matrices in the field of uses mentioned above.

Styrene based support matrices having HO-containing groups attached to pending phenyl rings have previously been prepared by copolymerising vinyl benzene containing a functionality that can be transformed to a hydroxy group after the polymerisation. In one alternative chloromethyl styrene has been polymerised followed by treatment with $OH^-$. Another alternative route has been conversion of residual vinyl groups in the polymer/copolymer to groups containing a hydroxy function.

Styryl substituted polyhydroxy polymers have previously been suggested for the manufacture of support matrices to be used in liquid chromatography, electrophoresis etc. See for instance WO 9731026.

In an International Type Search Report issued in connection with the SE priority application there have been cited:

Klavins et al (Latv. PSR Zinat. Akad. Vestis, Kim. Ser. (1986) (5) 618–24) disclose copolymers built up of chloromethyl vinyl benzene and divinyl benzene monomers. The copolymers have been reacted with pentaerytritol to replace the chloro atoms with —$OCH_2OCH_2C(CH_2OH)_3$ groups. These groups are then derivatized to crown ethers. The end products are used to support catalysis in organic synthesis;

JP patent application 1994-66638 (Koyama et al) describes in example 3 reaction of a 3,4-O-benzylidene-1,2 isopropylidene protected hexose with p-chloromethyl vinyl benzene. The corresponding polymer is used for mucosal drug administration.

JP patent application 1992-81142 (Shioji) gives in table form a polymer (34) with the monomeric unit —$CH_2$—$CH[C_6H_4CH_2N(CH_3)$  $(CHOH)_4$—$CH_2OH)]$—. The polymer is suggested to be used in dyeing cellulose fibers. No synthesis of the corresponding monomer is given.

JP patent application 1991-276275 (Watanabe et al) discloses porous 2,3-dihydroxypropyl 4-vinyl benzyl ether divinylbenzene copolymer microbeads obtained by hydrolysis of the corresponding epoxy microbeads (example 6). The microbeads are useful intermediates in preparing functional resins. No synthesis of 2,3-epoxypropyl 4-vinyl benzene is given.

There are also a number of articles by Kobyashi A and/or Akaike T etc that disclose polymers with monomeric units N-p-vinylbenzyl-O-beta-D-galactopyranosyl-D-gluconamide and the like. See for instance Cho C S et al., J. Biomater. Sci. Polym. Ed. 7(12) (1966) 1097–1104.

OBJECTS OF THE INVENTION

A first object is to provide new monomers that are simple to synthesize and/or groups that upon polymerisation easily can be transformed to storage-stable groups.

A second object is to provide alternative monomers that can be used in emulsion polymerisation and particularly in suspension polymerisation for the production of particles, such as beads, that may be porous or non-porous.

A third object is to provide alternative methods for the manufacture of support matrices carrying unprotected hydroxy groups and/or protected hydroxy groups, both of which are bound via an aryl structure to a cross-linked hydrocarbon backbone [—$(CH_2CH_2)_n$—].

A fourth object is to provide alternative methods for the manufacture of rigid matrices.

A fifth object is to provide alternative matrices that contain hydroxy groups for derivatization and grafting.

A sixth object is to provide alternative water-insoluble but hydrophilic support matrices.

A seventh object is to provide alternative matrices for each of the uses given above.

An eighth object is a method for the manufacture of beads having open pores and hydroxy groups on their pore surfaces (skin-less porous hydroxy beads). The method comprises bead polymerisation of a mixture containing one or more monomers carrying a single polymerisable unsaturation and one or more monomers carrying two or more polymerisable unsaturated groups.

THE INVENTION

A first aspect of the invention is a novel monomer that meets the above-mentioned objects and can be used for the manufacture of support matrices in one or more of the fields mentioned above. The monomer is a vinyl aromatic monomer comprising one or more vinyl groups and complies with the formula:

$$R\text{—}B\text{—}Ar(\text{—}CH\text{=}CH_2)_n \qquad (1)$$

The main characteristic feature is that the atom in B attaching directly to R is a heteroatom selected amongst thioether sulphur or ether oxygen. The preferred variants encompass that (a) the heteroatom is selected from thioether sulphur or ether oxygen and/or (b) R is a residue from a polyol containing an odd number of hydroxy groups, one of which is used for linkage to R while the remaining hydroxy groups are protected or unprotected.

Ar is an aromatic ring (arylene group), preferably a benzene ring (phenylene group). Ar may also be a heteroarylene, for instance a π-electron excessive variant, preferably having five or six ring atoms, preferably the former. There are typically two, three, four or more atoms between R—B and the vinyl group, with preference for three.

n is an integer >0, in particular one or two. In case n is 2, two vinyl groups shouldn't be located ortho to each other.

B is a bridge structure comprising a chain consisting of 1–10 atoms. The chain atoms are selected among $sp^3$-, $sp^2$- and sp-hybridised carbons, and the heteroatoms: ether oxygen, thioether sulphur, and amino nitrogens. In the chain there is a heteroatom attaching B to R (i.e. the chain terminal binding to R is one of the heteroatoms mentioned). When two or more heteroatoms are present, there are at least two carbon atoms between two heteroatoms. In the preferred cases the chain in B linking R and Ar together contains 1–8 atoms, such as 1–5 atoms. In preferred variants, the chain in B has one or two carbon atoms or is represented by a thioether or ether group for binding R to Ar. The chain may carry groups selected from hydrogen and lower alkyl, such as $C_{1-5}$ alkyl. The chain may be part of a cyclic bivalent group linking R and Ar together.

R is a $(C_{2-30})$-hydrocarbon group carrying two or more protected or unprotected hydroxy groups (polyhydroxy hydrocarbon group). Carbon atoms in protecting groups are not included in $C_{2-30}$. In preferred variants there are $\leq 10$ hydroxy groups. The $(C_{2-30})$-hydrocarbon group may be straight, branched or cyclic. It may contain an aromatic structure, such as phenylene, and/or contain an alkylene chain. R preferably comprises 2, 3, 4, 5, 6, 7 or more carbon atoms. The longest carbon chain (not including a protected hydroxy group) in the $(C_{2-30})$-hydrocarbon group may be interrupted at at least one position by a thioether sulphur or an ether oxygen. No more than one heteroatom (preferably oxygen or sulphur) is linked to one and the same carbon atom in R, or there is at most one carbon-heteroatom bond to each carbon in R groups in which the hydroxy groups are protected or unprotected. In this context double bonds are counted as two bonds. Typically the $(C_{2-30})$-hydrocarbon group has 2–10 carbon atoms).

There is an even number of protected or unprotected hydroxy groups, such as two, four, six, eight or ten such groups, in the preferred $(C_{2-30})$-hydrocarbon group. In the preferred variants, the hydroxy groups that are either protected or unprotected, are separated by a chain of two or three carbon atoms. In this latter case a protecting group should be bivalent forming 5- or 6-membered ring structure with atoms in the unprotected form of the $(C_{2-30})$-hydrocarbon group. See below. In the preferred variants of R all or none of the hydroxy groups are protected.

Preferred Rs include monovalent residues derived from sugar alcohols (sugar alcohol residues) with 3–6 carbon atoms (3–6 hydroxy groups) with particular emphasis of residues from sugar alcohols that have 3 and 5 carbons (3 and 5 hydroxy groups). By the term residue is in this context meant the sugar alcohol minus the hydroxy group used for linking R to B, preferably a terminal hydroxy. The remaining hydroxy groups may be in protected or unprotected forms. The most useful residues are those deriving from glycerol (glyceryl), arabitol (arabityl) and xylitol (xylityl) with the free valence being in a terminal position.

By a hydroxy protecting group is contemplated a group that can remain essentially intact during polymerisation and thereafter removed or cleaved off selectively, typically by hydrolysis or reduction. Since the monomer only contains relatively stable links (C—C, C=C, C≡C, C—H, ether, thioether) this often gives a great versatility in selecting suitable protecting groups. See for instance Protecting Groups i Organic Synthesis, Ed. Greene, John Wiley & Sons, Inc., Chapter 11 (1991) 10–142.

The hydroxy protected group in the monomer of formula (1) may have the formula $$\text{—O—}R_p \text{ or —O—}R_{p'}\text{—O—} \qquad \text{(2a and 2b, respectively)}$$

in which $R_p$ and $R_{p'}$ are protecting groups.

$R_p$ is a monovalent group and may be selected among acyl groups, in particular $C_{1-10}$ acyls, including —CO—O—$R_{p''}$ where $R_{p''}$ is a $C_{1-9}$ hydrocarbon group. Acyl groups may have hydrogens replaced with eletron-withdrawing groups and other groups facilitating deprotection.

$R_{p'}$ is a divalent group and is attached at two positions in R, which means that there will be 5- or 6-membered ring structures as discussed above. In these cases $R_{p'}$ may contain a chain of one or two atoms binding to the two oxygens in —O—$R_{p'}$—O—. In the one carbon atom case, —O—$R_{p'}$—O— may be —O—CO—O— or part of an acetal or of a ketal group, i.e. groups that can be hydrolysed. Examples of preferred $R_{p'}$s are alkylidenes, such as methylene, ethylidene (CH₃CH=), isopropylidene, cyclohexylidene etc.

As apparent from the above epoxy groups, such as in glycidyl, are not considered to be a protected form of two vicinal hydroxy groups.

The protecting group preferably has a hydrophobicity such that the monomer of formula (1) becomes essentially insoluble in water (polymerisation in suspensions often demands that the monomer shall partition to the oil phase).

The second aspect of the invention encompasses a method for the manufacture of a support matrix as defined under the heading "Technical Field" above. The method comprises the step of copolymerising one or more monomers carrying one vinyl groups (monomer I) with one or more monomers carrying two or more vinyl groups (monomer II, cross-linking monomer). The method is characterized in that a part of the vinyl monomers (monomer III) is of the same kind as defined for the monomer of formula 1 above and closely related forms thereof.

Monomer III thus has the formula $$R'\text{—}B'\text{—}Ar(\text{—}CH\text{=}CH_2)_n \qquad (3)$$

Ar and n have the same meaning as above. R' is selected from the same groups as R but the $(C_{2-30})$-hydrocarbon group may in addition carry amino, aldehyde, carboxy group, amido, ester and other hydrophilic groups containing one or more heteroatoms (such as oxygen and nitrogen), and also one single hydroxy group. If needed, hydroxy groups and also other groups may be in protected form. B' have the same meaning as above but may in addition be nothing (single bond).

In the case the polymerisation is run as a suspension/dispersion polymerisation in which one of the phases is a water phase, hydrophilic groups should be protected in monomer III. Both protected and unprotected forms of monomer III may be used in other types of polymerisations.

In the case monomer III has been used in protected form, the hydroxy-protecting groups may be removed to expose free hydroxy groups subsequent to the polymerisation. The polyhydroxy polymer may be further processed by transforming all or part of the hydroxy groups to a desired functionality. This also applies for protected forms of the polyhydroxy polymers. Also other transformations may be carried out.

Suspension/dispersion polymerisation with one of the phases being a water phase in combination with hydroxy groups and the like in protected form and deprotection subsequent to polymerisation will enable the production of so called skin-less porous beads. These beads will be functionalized with hydroxy groups and the like on their inner/pore and outer surfaces.

Monomer III may be a mixture of monomers having different R'—B' groups (R'$_1$—B'$_1$, R'$_2$—B'$_2$, R'$_3$—B'$_3$ ... ).

Monomer III is part of monomer I and/or monomer II.

Compounds to be used as monomer I are acrylates, methacrylates, acrylamides, methacrylamides, acrylnitriles, methacrylnitriles, vinyl aromatics like monovinyl benzenes such as unsubstituted or substituted variants thereof (preferably meta or para isomers), etc. Monomer I may also be an alkyl vinyl benzene, for instance with a $C_{1-10}$ alkyl substituent, such as ethyl, attached to the aromatic ring. Suitable monomers to be used as monomer I includes monomers of formula (3) in which n equals to 1.

Compounds to be used as monomer II are bisforms of acrylates and methacrylates, acrylamides and methacrylamides, divinyl aromatics like various forms of divinyl benzenes (preferably meta or para forms) etc. Corresponding forms having more than two vinyl groups may in principle also be used. Monomer II acts as a cross-linker. Monomer II may also be alkylated forms and ether forms of the divinyl monomers just mentioned. Suitable monomers to be used as monomer I includes monomers of formula (3) in which n equals to 2 or more, with preference for 2.

Monomer I may be a mixture of various individual monomers having one vinyl group. Monomer II may be a mixture of individual monomers having two or more vinyl groups. In a typical polymerisation mixture the %-amounts are:

monomer I: $\geq 0.5\%$ such as $\geq 20\%$ and $\leq 99.5\%$, such as $\leq 95\%$ monomer II: $\geq 0.5\%$ such as $\geq 5\%$ and $\leq 99.5\%$, such as $\leq 80\%$ monomer III: $\geq 0.5\%$ and $\leq 80\%$.

Increasing the %-amount of monomer II will increase the rigidity of the final polymer and reduce the ability to swell in organic solvents.

The exact selection of %-amounts will depend on the use contemplated of the support matrix.

For uses in which the matrix does not need to withstand pressure, for instance from a liquid flow, typical %-amounts are:

monomer I: $\geq 95\%$ such as $\geq 98\%$ and $\leq 99.5\%$ monomer II: $\geq 0.5\%$ and $\leq 5\%$ such as $\leq 2\%$ monomer III: $\geq 5\%$ such as $\geq 15\%$ and $\leq 80\%$ such as $\leq 50\%$.

The matrices obtained with these compositions are of particular importance for most kinds of step-wise solid phase synthesis of organic compounds, except for nucleic acid synthesis.

For uses in which the matrix need to withstand pressure, typical %-amounts are:

monomer I: $\geq 10\%$ such as $50\%$ and $\leq 90\%$ such as $\leq 80\%$ monomer II: $\geq 5\%$ such as $\geq 10\%$ and $\leq 80\%$ such as $\leq 50\%$ monomer III: $\geq 0.5\%$ such as $\geq 2\%$ and $\leq 40\%$ such as $\leq 35\%$ and even $\leq 20\%$.

The matrices obtained with these compositions are of particular importance for applications in which a matrix is placed in a column/vessel and a liquid flow containing reagents is allowed to pass through. Typical uses are chromatographic applications and solid phase synthesis of nucleic acids.

The percentages given above are w/w and calculated on the total amount of polymerisable vinyl monomers in the polymerisation mixture.

The polymerisation conditions will depend on the vinyl monomers used and on demands on the final polymer. One of the most preferred kinds of polymerisations for the invention utilizes free radicals and an initiating system.

Initiating systems are electron irradiation, γ-irradiation, radical initiators etc. Typical initiators are chemical, thermal and irradiation initiators. Thermal initiators are often preferred. They have their best efficiency in the range of 50–90° C. Thermal initiators active at lower temperatures often require cooling when preparing mixtures to be polymerised.

Thermal/chemical initiators are azo compounds (for instance 2,2'-azobis(2,4-dimethylvaleronitrile), azoisonitriles, peroxides (for instance benzoylperoxide), persulphates.

Redox systems may also be used, for instance Fenton's reagent (hydrogen peroxide+$Fe^{2+}$).

Polymerisation may take place in conventional o/w-emulsions/suspensions and dispersions to give more or less spherical particles provided the appropriate conditions are applied as known in the field. Similarly also bulk polymerisation may be utilized, possibly with subsequently disintegrating the block into particles, if so found appropriate. For polymerisations in emulsions and suspensions in which one of the phases is an aqueous phase, such as a water phase or an otherwise polar phase, the hydroxy groups in the monomers should be protected as well as other hydrophilic groups that may be present.

Emulsifiers and stabilizers typical for polymerisations in emulsions, suspensions and dispersions can also be used in the present invention. Well known emulsifiers and stabilizers are sodium dodecyl sulphate, alkylated oligo ethylene glycols, cellulose derivatives etc.

One can also envisage that polymerisations are carried out in so called inverse emulsions (w/o-emulsions) in which the conditions have been selected such that the water droplets break up to a macroporous network having open spherical cavities communicating with each other (water act as a porogen). See for instance EP 60,138 and U.S. Pat. No. 5,200,433. This can be extended to so called w/o/w emulsions in which the inner w/o-emulsion is in form of drops of so called high internal phase emulsions (HIPEs). See WO 9531485.

A particular important variant for manufacturing the particles according to the invention utilizes seed particles, and preferably includes a first step comprising swelling the seed particles and then a second step comprising uptake of monomers before polymerisation. See for instance U.S. Pat. No. 4,336,173 which is hereby incorporated by reference.

By including an appropriate porogen into a polymerisation mixture, porous materials in form of particles/beads and monolithic plug material can be accomplished. Porogens are compounds that in some way separate out and forms channels/pores when the polymer is formed. Porogens may be in form of liquids, solids or gases and shall be possible to remove after polymerisation. Porogens in form of liquids are typically capable of completely dissolving the monomers used but not the polymer chain created. This means that the polymer chains will separate out and form a polymer material containing a pore system filled with the porogen. The characteristics of the pore system will depend on the amount and type of porogen. In general porogens with solubility parameter values near the solubility parameter value of the polymer results in elastic gel-like porous material with relatively high proportion of smaller pores. Aromatic solvents, such as toluene, xylene, mesitylene etc, have the potential to give this effect in case vinyl aromatics are polymerised.

The use of porogens with larger differences between the solubility parameter value of the porogen and of the polymer often results in more rigid porous material with a lower proportion of smaller pores. This effect will, for vinyl aromatics be obtained with, for instance, alcanols and aliphatic hydrocarbons as porogens. Often used porogens of this type have been alkanes, such as heptane, alkanols, such as decanol. Also mixtures of liquid compounds have been used as porogens.

Polymers may also be used as porogens.

The porous materials obtained may have pore sizes, pore volumes and pore surface areas as known in art for vinyl polymers. The pore size diameters thus may be within the interval of 10 Å–1000 µm, typically within 10 Å–100 µm. The optimal selection of pore diameters typically depends on the use contemplated and can, for instance, be selected according to rules known in the field.

In case the material is in particle form, its mean particle size typically is in the range of 1–1000 µm, preferably 3–1000 µm or 3–500 µm, i.e. particle sizes that normally are not obtained by emulsion polymerisation. The particles may have an irregular shape, such as obtained by disintegrating blocks obtained from bulk polymerisations, or spherical (beaded) as obtained from polymerisation in suspensions. The particles may be monodisperse or polydisperse, with monodisperse particle populations having more than 95% of the particles within the mean diameter ±5%.

Subsequent to polymerisation all or part of the protected hydroxy groups may be transformed by methods known in the field to

—O—A—X in which (a) A is an organic bridge structure and
(b) X is a structure containing
   (i) one or more reactive groups capable of reacting with a substance carrying a nucleophilic or an electrophilic group or with a free radical to covalently attach said substance or a part thereof to said support matrix, or
   (ii) one or more groups that can be transformed to such a reactive group, or
   (iii) a member of an affinity pair mediating affinity binding of the other member of the pair.

Typically A comprises a stable organic chain in which there are one or more organic structural elements selected from (a) straight, branched or cyclic hydrocarbon chains comprising 1–20 carbon atoms, (b) ether, (c) thioether, (d) amide structures, (e) ester, (f) azo, (g) secondary or tertiary amine structures, etc. The preferred structures typically have a hydrolytic stability that is comparable to or higher than acetamide, for instance. In some applications it may be advantageous to include structures having a lowered stability in order to enable selective cleavage at a certain location.

By the term "stable" above is contemplated that the organic chain does not unintentionally deteriorate or react with any of the groups present in the inventive support matrix or under the conditions applied during its use.

Reactive groups as defined above and present in structure X are well known in the field, for instance hydroxy, amino, thiol, carboxy etc or activated forms of these groups.

Structure X may be a nucleotide or deoxynucleotide or a nucleic acid (DNA, RNA, oligonucleotide, and analogues such as PNA and LNA and protected forms) which is linked to the support as known in the field.

X may also be an amino acid or an oligopeptide, including mimetics and protected forms, linked at its carboxy end to a support matrix as defined above.

X may also be a member of a so called affinity pair and used to affinity bind ("affinity adsorb") the other member of the pair to the support matrix. Well-known affinity pairs are
(a) positively and negatively entities (ion exchange; the immobilised entity being selected among primary, secondary, tertiary and quaternary ammonium, sulphonate, sulphate, phosphonate, phosphate, carboxy etc groups),
(b) antibodies and antigens/haptens,
(c) lectins and carbohydrate structures,
(d) IgG binding proteins and IgG,
(e) pair of hydrophobic groups,
(f) polymeric chelators and chelates,
(g) complementary nucleic acids, etc.

Affinity members also include entities participating in catalytic reactions, for instance enzymes, enzyme substrates, cofactors, cosubstrates etc. Members of affinity pairs include chemically produced mimetics of bioproduced forms.

The third aspect of the invention is a support matrix comprising a hydrocarbon backbone [—($CH_2CH_2$)$_n$—]. The support matrix is characterized in that there are
(A) a plurality of inter- and/or intrachainly cross-linking bridges substituting hydrogens in the backbone and
(B) a plurality of identical or different groups R'—B'—Ar—(R'$_1$—B'$_1$—Ar—, R'$_2$—B'$_2$—Ar—, R'$_3$—B'$_3$—Ar— . . . ) in which R'—B'—Ar, R'$_1$—B'$_1$—Ar—, R'$_2$—B'$_2$—Ar— . . . have the same meaning as above.

The cross-linking bridges may derive from vinyl monomers having two or more vinyl groups and included in the polymerisation process. The cross-linking bridges may also have been accomplished after polymerisation, for instance by the use of bifunctional electrophilic/nucleophilic cross-linking agents.

The support matrix of this aspect may also comprise a plurality of identical or different R" groups that are
(a) substituting a respective hydrogen in the backbone and
(b) comprising a group —A—X as defied above.

Except for the presence of —A—X, the R" groups may be selected among the same groups as R'—B' in which —A—X substitutes a hydrogen in a hydroxy group.

What has been outlined above for the second aspect of the invention in regard to physical appearance, such as monolithic or particle forms, particle sizes, pore geometry and pore sizes etc, also apply to the third aspect of the invention.

A fourth aspect of the invention is the use of the support matrix prepared by the method of the invention in the various fields indicated in the introductory part above. In principle the various steps for each respective use are per se known, without exclusion of future developments.

In case the support matrices as defined above are used for affinity adsorption, X is a member of an affinity pair as defined above. The use comprises bringing the support matrix and a liquid, typically an aqueous liquid, containing the other member of the affinity pair in contact with each other. The conditions are selected to promote affinity binding and are in principle regarded as per se known in the field. Subsequently the support matrix is separated from the liquid and if so desired the affinity adsorbed member can be released and further processed.

The invention will now be illustrated by a number of non-limiting patent examples. The invention is further defined in the attached patent claims.

EXPERIENTAL PART

DRAWINGS

SYNTHESIS OF PROTECTED MONOMER

Figure 1:
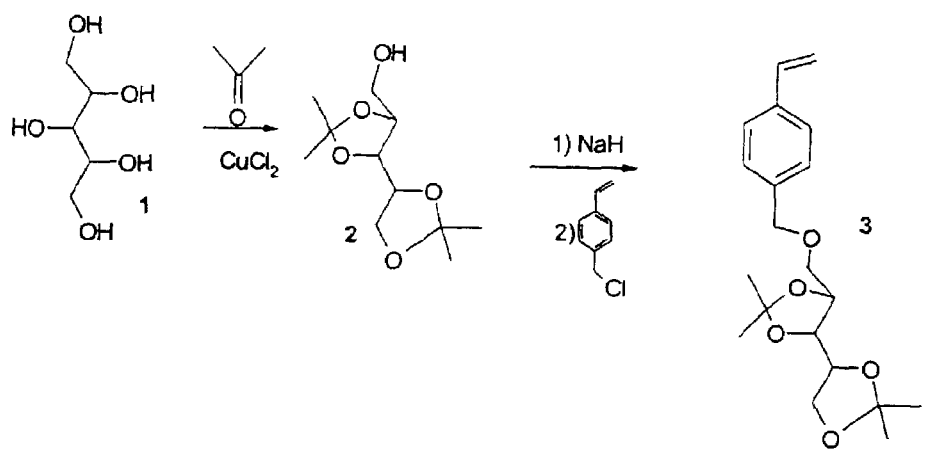
FIG. 1 illustrates the synthesis of a protected vinyl monomer according to the invention.
Figure 2:
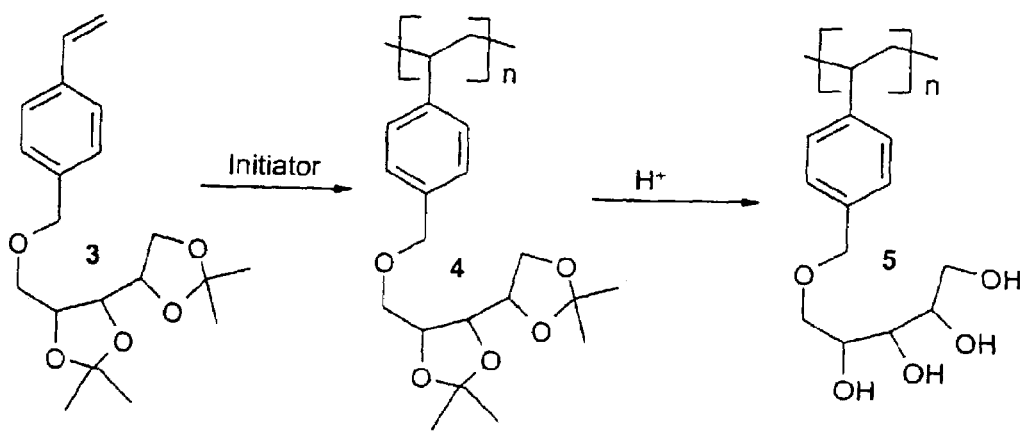
FIG. 2 illustrates the polymerisation utilizing a protected form of the inventive vinyl monomer and deprotecting of the hydroxy groups.

Isopropylidenation of xylitol according to Tipson & Cretcher, J. Org. Chem. 8 (1943) 95: 15 g of xylitol (1) (Aldrich), 20 g of $CuSO_4$ (Merck) and 0.2 mL of $H_2SO_4$ in 200 mL of acetone (APB-grade) were stirred for 90 h. The blue $CuSO_4(H_2O)x$ was filtered off and washed with 2×50 mL of acetone. About 1 g of $NaHCO_3$ (powder) was added and the mixture was stirred for 1 h. After filtration the acetone was evaporated on a rotavapor to give 21.4 g of crude diisopropylidene xylitol (2).

Reaction with vinylbenzyl chloride: The crude product from 1. Was dissolved in 30 mL of THF and added dropwise to 4.0 g of 60% NaH dispersion suspended in 20 mL of THF (after washing with pentane to remove the mineral oil). After the $H_2$ evolution ceased (warm carefully to 50° C. after completed addition) 1 equiv. of 90% vinyl benzyl chloride (VBC) was added dropwise while chilling in an ice bath. After 4 H reaction at 50° C. the mixture was left overnight. Ethanol was added to destroy any residual NaH. Brine (200 g NaCl in 1 L of $H_2O$) and diethyl ether were added and the inorganic phase was extracted with several portions of $Et_2O$. The combined organic phases were extracted with brine until neutral. The organic phase was dried over $K_2CO_3$/$Na_2SO_4$, the solvent evaporated to give 16.0 g of crude (3).

Polymerisation

| Water phase: | 130 g 5% PVA Mowiol 40-88 |
| --- | --- |
| | 120 g 1.4 M NaCl |
| Organic Phase: | 30 g tert-amyl alcohol |
| | 12 g monomer 3 (Scheme 1) |
| | 6 g DVB (63%) |
| | 0.3 g AIBN (azobisisobuteronitrile) |
| Reaction flask: | 250 mL round bottom with four-necked cap |
| Stirrer: | 40 mm turbine stirrer |

With stirring (120 rpm) the water phase was charged to the reaction flask. The organic phase was mixed separately and charged to the reaction flask. The stirring speed was raised to 175 rpm and the temperature of the water bath was raised to 70 C. After 4 h reaction, the formed beads were washed with varm water, acetone, distilled water and dried in vacuum overnight. The bead size was mainly 200–400 µm. According to IR there was a small absorption corresponding to a hydroxyl.

The isopropylidene groups were removed by 80% acetic acid. Thus in a 250 mL round bottomed reaction flask equipped with a teflon coated turbine stirrer, 5 g of polymer beads were slurried in the acid at 65° C. during 2 h. The beads were washed with distilled water on the glass filter and dried in vacuum overnight. The IR shows a marked increased amount of hydroxyls.

What is claimed is:

1. In a method for producing a support matrix by copolymerising one or more monomers having one vinyl group (monomer I) with one or more vinyl monomers having two or more vinyl groups (monomer II), the improvement comprising adding a vinyl monomer (monomer III) having the formula:

R'—B'—Ar(—CH=CH$_2$)$_n$ (3)

in which
  Ar is an aromatic ring (arylene group);
  n is an integer >0;
  B' is a bridge structure selected from a single bond and bivalent groups comprising a chain of atoms linking R' to Ar and consisting of 1–10 atoms, selected from carbons and the heteroatoms: ether oxygen, thioether sulphur or amino nitrogen, with the proviso that the terminal atom in B' which is attached to R' is one of the heteroatoms;
  R' is a ($C_{2-30}$)-hydrocarbon group carrying two or more protected hydroxy groups; and
  copolymerizing the monomers.

2. The method of claim 1, wherein the hydroxy groups of monomer III are protected by groups rendering monomer III insoluble in water and the copolymerisation is run as a suspension polymerisation.

3. The method of claim 1, wherein the copolymerisation is run under conditions resulting in beads.

4. The method of claim 1, wherein the mixture of vinyl monomers includes a porogen.

5. The method of claim 1, wherein the vinyl monomers are selected among acryl, methacryl monomers and vinyl benzene monomers.

6. The method of claim 1, further comprising deprotecting protected hydroxy groups subsequent to the copolymerisation step.

7. A support matrix comprising a hydrocarbon-backbone having the repeating unit —$CH_2CH_2$—, having
   (A) a plurality of inter- and/or intrachainly cross-linking bridges substituting hydrogens in the backbone and
   (B) a plurality of identical or different groups of the structure R'—B'—Ar—    (4)

substituting a respective hydrogen in the backbone, wherein
   Ar is an aromatic ring (arylene group);
   B' is a bridge structure selected from a single bond and bivalent groups comprising a chain of atoms linking R' to Ar and consisting of 1–10 atoms, selected from carbons and the heteroatoms: ether oxygen, thioether sulphur or amino nitrogen, with the proviso that the terminal atom in B' which is attached to R' is one of the heteroatoms; and
   R' is a ($C_{2-30}$)-hydrocarbon group carrying two or more protected hydroxy groups.

8. The support matrix of claim 7, wherein the support matrix is in the form of a monolithic plug or particles.

9. The support matrix of claim 7, wherein the support matrix is in the form of beads.

10. The support matrix of claim 7, wherein the support matrix is porous.

11. The support matrix of claim 7, further including plurality of R" groups each of which
   (a) substituting a respective hydrogen in the hydrocarbon backbone and
   (b) comprising a group —A—X in which
      X is a member of an affinity pair mediating affinity binding of the other member of the pair; and
      A is an inert bridge structure.

* * * * *